United States Patent
Scheib

(10) Patent No.: US 6,733,499 B2
(45) Date of Patent: May 11, 2004

(54) CATHETER HAVING CIRCULAR ABLATION ASSEMBLY

(75) Inventor: Mark S. Scheib, LaVerne, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 10/118,680

(22) Filed: Apr. 9, 2002

(65) Prior Publication Data

US 2003/0163127 A1 Aug. 28, 2003

Related U.S. Application Data

(60) Provisional application No. 60/360,431, filed on Feb. 28, 2002.

(51) Int. Cl.[7] .............................................. A61B 18/18
(52) U.S. Cl. ......................................... 606/41; 128/898
(58) Field of Search ............................... 606/41, 27–28, 606/32–38, 46–52

(56) References Cited

U.S. PATENT DOCUMENTS

| | | | | |
|---|---|---|---|---|
| 3,635,212 A | * | 1/1972 | Watanabe et al. | 600/348 |
| 3,862,627 A | * | 1/1975 | Hans, Sr. | 600/348 |
| 4,777,955 A | | 10/1988 | Brayton et al. | |
| 4,882,777 A | | 11/1989 | Narula | |
| 4,920,980 A | | 5/1990 | Jackowski | |
| 4,960,134 A | | 10/1990 | Webster, Jr. | |

(List continued on next page.)

FOREIGN PATENT DOCUMENTS

EP 0 499 491 A2 8/1992

*Primary Examiner*—Roy D. Gibson
*Assistant Examiner*—Peter J Vrettakos
(74) *Attorney, Agent, or Firm*—Christie, Parker & Hale, LLP

(57) ABSTRACT

A catheter particularly useful for ablation lesions within a tubular region of or near the heart is provided. The catheter comprises an elongated flexible tubular catheter body having an axis and proximal and distal ends. An ablation assembly is mounted at the distal end of the tubular body. The ablation assembly has a preformed generally circular curve having an outer surface and being generally transverse to the axis of the catheter body. The ablation assembly comprises a flexible tubing having proximal and distal ends that carries a tip electrode at its distal end. An electrode lead wire extends through the catheter body and into the ablation assembly and has a distal end connected to the tip electrode. In use the distal end of the catheter is interested into the heart of a patient. At least a portion of the outer circumference of the generally circular curve is contacted with the inner circumference of the tubular region so that the tip electrode is in a first position in contact with tissue along the inner circumference. The tip electrode is used to ablate tissue at the first position. The ablation assembly can then be rotated so that the tip electrode is in a second position in contact with tissue along the inner circumference different from the first position, and the tip electrode is used to ablate tissue at the second position. This procedure can be repeated to form a lesion of the desired length along the inner circumference.

20 Claims, 7 Drawing Sheets

U.S. PATENT DOCUMENTS

| | | |
|---|---|---|
| 4,984,581 A | 1/1991 | Stice |
| 5,170,787 A | 12/1992 | Lindegren |
| 5,255,679 A | 10/1993 | Imran |
| 5,263,493 A | 11/1993 | Avitall |
| 5,275,162 A | 1/1994 | Edwards et al. |
| 5,327,905 A | 7/1994 | Avitall |
| 5,354,297 A | 10/1994 | Avitall |
| 5,383,923 A | 1/1995 | Webster, Jr. |
| 5,445,148 A | 8/1995 | Jaraczewski et al. |
| 5,487,385 A | 1/1996 | Avitall |
| 5,545,200 A | 8/1996 | West et al. |
| 5,549,581 A | 8/1996 | Lurie et al. |
| 5,582,609 A * | 12/1996 | Swanson et al. ............... 606/39 |
| 5,617,854 A | 4/1997 | Munsif |
| 5,626,136 A | 5/1997 | Webster, Jr. |
| 5,642,736 A | 7/1997 | Avitall |
| 5,673,695 A | 10/1997 | McGee et al. |
| 5,680,860 A | 10/1997 | Imran |
| 5,730,127 A | 3/1998 | Avitall |
| 5,755,760 A | 5/1998 | Maguire et al. |
| 5,797,905 A | 8/1998 | Fleischman et al. |
| 5,800,428 A | 9/1998 | Nelson et al. |
| 5,827,278 A | 10/1998 | Webster, Jr. |
| 5,836,947 A | 11/1998 | Fleischman et al. |
| 5,860,920 A | 1/1999 | McGee et al. |
| 5,865,800 A | 2/1999 | Mirarchi et al. |
| 5,879,295 A | 3/1999 | Li et al. |
| 5,882,333 A | 3/1999 | Schaer et al. |
| 5,882,346 A | 3/1999 | Pomeranz et al. |
| 5,931,811 A | 8/1999 | Haissaguerre et al. |
| 5,935,102 A | 8/1999 | Bowden et al. |
| 5,938,694 A | 8/1999 | Jaraczewski et al. |
| 5,951,471 A | 9/1999 | de la Rama et al. |
| 5,984,909 A | 11/1999 | Lurie et al. |
| 5,997,526 A | 12/1999 | Giba et al. |
| 6,002,955 A | 12/1999 | Willems et al. |
| 6,035,224 A | 3/2000 | West |
| 6,064,902 A | 5/2000 | Haissaguerre et al. |
| 6,088,614 A | 7/2000 | Swanson |
| 6,090,104 A | 7/2000 | Webster, Jr. |
| 6,096,036 A | 8/2000 | Bowe et al. |
| 6,106,522 A * | 8/2000 | Fleischman et al. .......... 606/41 |
| 6,129,724 A | 10/2000 | Fleischman et al. |
| 6,146,381 A | 11/2000 | Bowe et al. |
| 6,162,219 A * | 12/2000 | Nilsson et al. ................ 606/41 |
| 6,169,916 B1 | 1/2001 | West |
| 6,325,797 B1 * | 12/2001 | Stewart et al. ................ 606/41 |

\* cited by examiner

CATHETER HAVING CIRCULAR ABLATION ASSEMBLY

CROSS-REFERENCE TO RELATED APPLICATION

This application claims priority of U.S. Provisional Patent Application No. 60/360,431, filed Feb. 28, 2002, the disclosure of which is incorporated herein by reference.

FIELD OF THE INVENTION

The present invention relates to an improved ablation catheter that is particularly useful for ablating in a tubular region of or near the heart.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. A common procedure involves ablating a lesion to interrupt the wavelets using one or more electrodes mounted on the distal end of a generally-straight catheter. This procedure works well, for example, when ablating a line of block in the atria. However, for tubular regions in or around the heart, this procedure is less effective. For example, when the line of block is to be made about a circumference of the tubular region, it is difficult to manipulate and control the distal end of a straight catheter so that it effectively ablates about the circumference. Accordingly, a need exists for an improved catheter that is particularly useful for such applications.

SUMMARY OF THE INVENTION

The present invention is directed to a catheter having a generally-circular ablation assembly mounted on its distal end that carries a tip electrode. In one embodiment, the catheter comprises an elongated flexible tubular catheter body having an axis and proximal and distal ends. An ablation assembly is mounted at the distal end of the tubular body. The ablation assembly has a preformed generally circular curve that is generally transverse to the axis of the catheter body comprising a flexible tubing having proximal and distal ends and carrying a tip electrode at its distal end. An electrode lead wire extends through the catheter body and into the ablation assembly and has a distal end connected to the tip electrode.

In use, the distal end of the catheter is inserted into the heart of a patient. At least a portion of the outer circumference of the generally circular curve is contacted with the inner circumference of the tubular region so that the tip electrode is in a first position in contact with tissue along the inner circumference. The tip electrode is used to ablate tissue at the first position. The ablation assembly can then be rotated so that the tip electrode is in a second position in contact with tissue along the inner circumference different from the first position, and the tip electrode is used to ablate tissue at the second position. This procedure can be repeated to form a lesion of the desired length along the inner circumference. This design permits the user to have more control when ablating about a circumference of a tubular region in or around the heart, e.g., a pulmonary vein, the coronary sinus, the superior vena cava, or the pulmonary outflow tract.

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
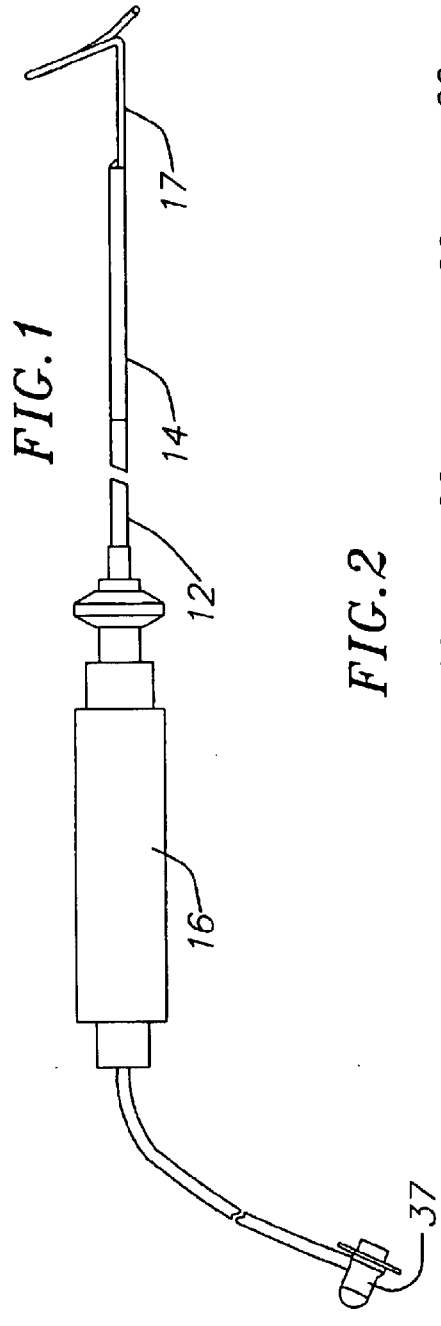
FIG. 1 is a perspective view of an embodiment of the catheter of the invention.

In a particularly preferred embodiment of the invention, there is provided a catheter having an ablation assembly at its distal end. As shown in FIG. 1, the catheter comprises an elongated catheter body 12 having proximal and distal ends, a intermediate section 14 at the distal end of the catheter body, a control handle 16 at the proximal end of the catheter body, and an ablation assembly 17 mounted at the distal end of the catheter to the intermediate section.

Figure 2:
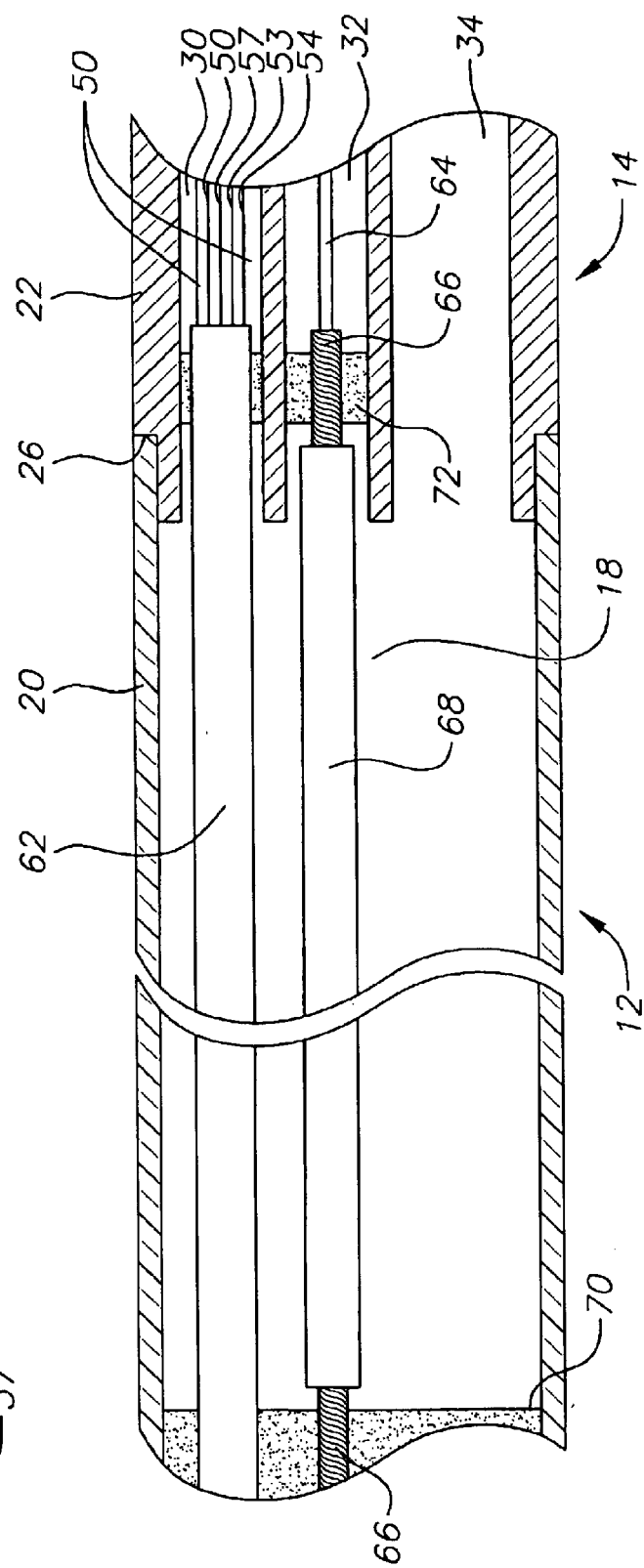
FIG. 2 is a side cross-sectional view of a catheter body according to the invention, including the junction between the catheter body and the intermediate section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably about 7 french. Likewise the thickness of the outer wall 20 is not critical, but is thin enough so that the central lumen 18 can accommodate a puller wire, one or more lead wires, and any other desired wires, cables or tubes. If desired, the inner surface of the outer wall 20 is lined with a stiffening tube (not shown) to provide improved torsional stability. A particularly preferred catheter has an outer wall 20 with an outer diameter of from about 0.090 inch to about 0.094 inch and an inner diameter of from about 0.061 inch to about 0.065 inch.

The intermediate section 14 comprises a short section of tubing 22 having three lumens. The first lumen 30 carries one or more lead wires 50 or other wires discussed further below, the second lumen 32 carries a puller wire 64, and the third lumen 34 carries a support member 24. The tubing 22 is made of a suitable non-toxic material that is preferably more flexible than the catheter body 12. A presently preferred material for the tubing 22 is braided polyurethane, i.e., polyurethane with an embedded mesh of braided stainless steel or the like. The size of each lumen is not critical, but is sufficient to house the lead wires, puller wire or support member.

The useful length of the catheter, i.e., that portion that can be inserted into the body excluding the ablation assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIG. 2. The proximal end of the intermediate section 14 comprises an outer circumferential notch 26 that receives the inner surface of the outer wall 22 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 3:
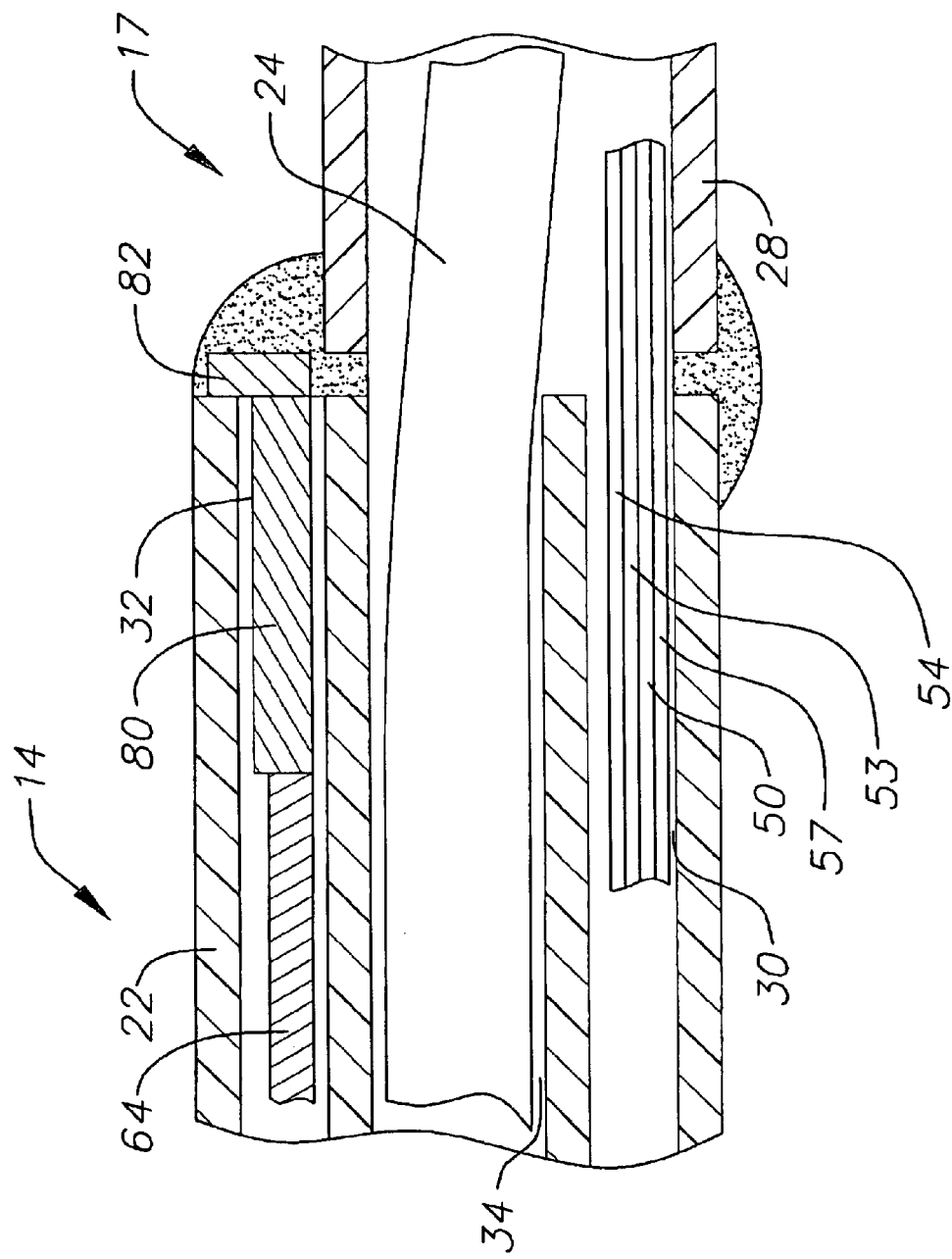
FIG. 3 is a side cross-sectional view of the intermediate section, including the junction between the intermediate section and the ablation assembly.
Figure 4:
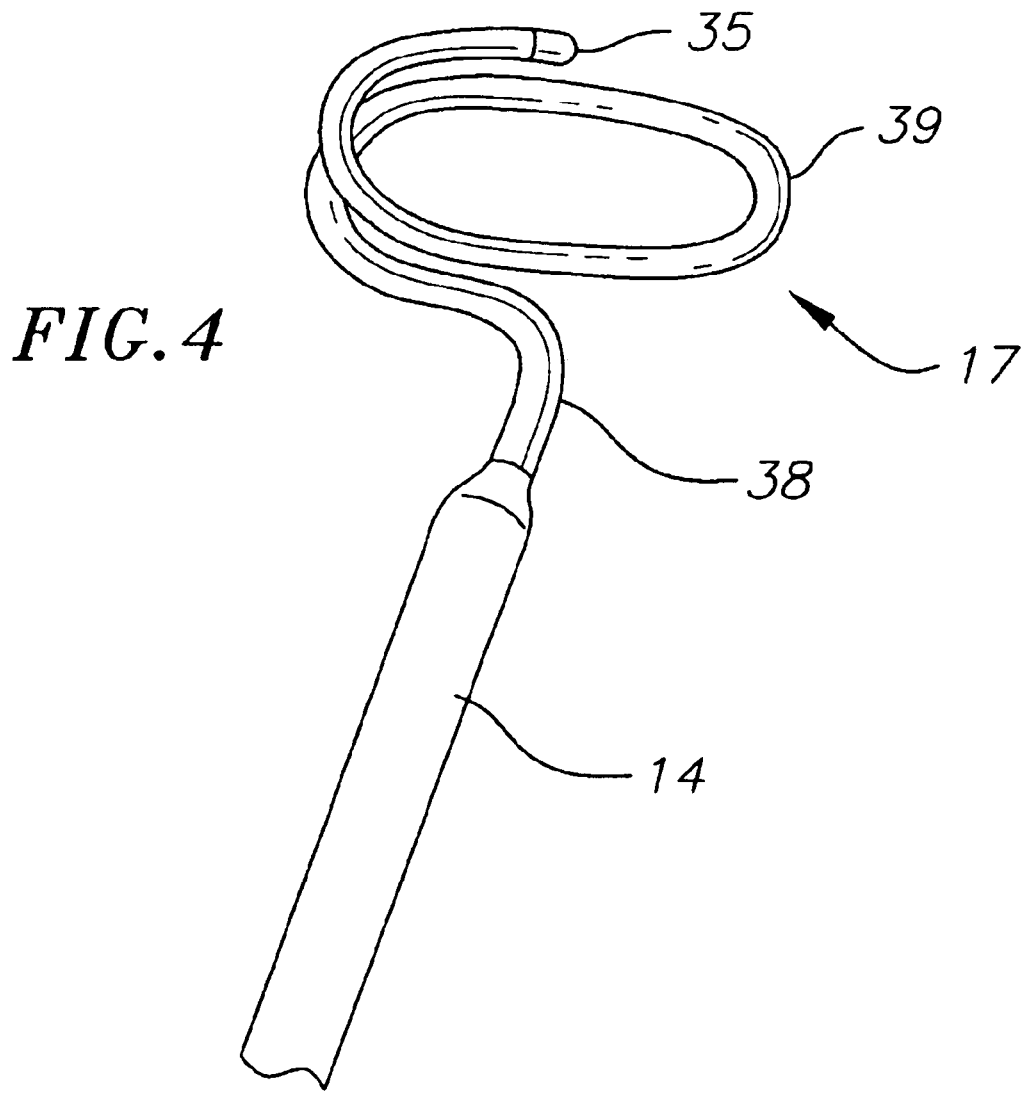
FIG. 4 is a schematic perspective view of an ablation assembly according to the invention.

At the distal end of the intermediate section 14 is the ablation assembly 17, as shown in FIGS. 3 to 7. In the depicted embodiment, the ablation assembly 17 comprises the distal end of the support member 24 covered by a non-conductive covering 28. In the embodiment of FIG. 4, the ablation assembly 17 comprises a generally straight proximal region 38 and a generally circular main region 39 that is generally transverse to the catheter body. The proximal region 38 is mounted on the intermediate section 14, as described in more detail below, so that its axis is generally parallel to the axis of the intermediate section. In this embodiment, the proximal region 38 is generally at the center of the generally circular main region 39. The proximal region 38 preferably has an exposed length, i.e., not contained within the intermediate section 14, ranging from about 3 mm to about 12 mm, more preferably about 3 mm to about 8 mm, still more preferably about 5 mm, but can vary as desired.

The generally circular main region 39 does not have to form a complete circle, but should be at least about 180°, e.g., a semi-circle, more preferably at least about 270°, still more preferably at least about 320°. In the preferred embodiment, the generally circular main region 39 forms at least a complete circle, e.g., is at least 360°. If desired, the generally circular main region can comprise more than one loop or circle, so that it has, for example, a spiral or conical shape. The generally circular main region 39 is generally transverse to the catheter body 12 and intermediate section 14, and preferably forms an angle with the catheter body ranging from about 80° to about 100°, more preferably about 90°. The generally circular main region 39 has an outer diameter preferably ranging from about 2 mm to about 40 mm, more preferably from about 10 mm to about 25 mm, still more preferably from about 12 mm to about 20 mm, even more preferably about 15 mm.

Figure 5:
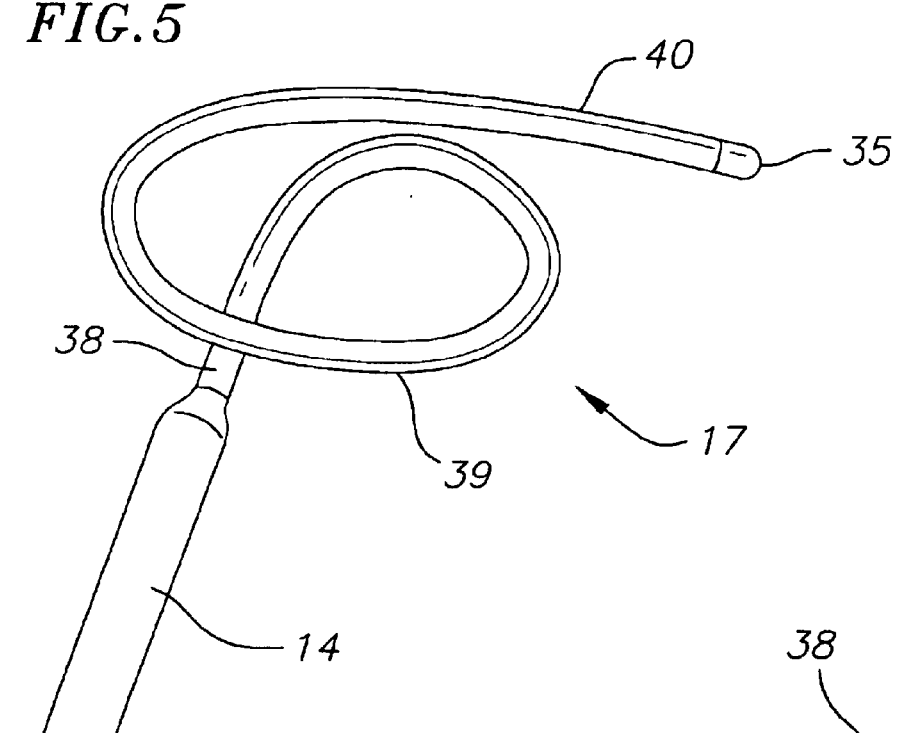
FIG. 5 is a schematic perspective view of an alternative ablation assembly according to the invention.
Figure 6:
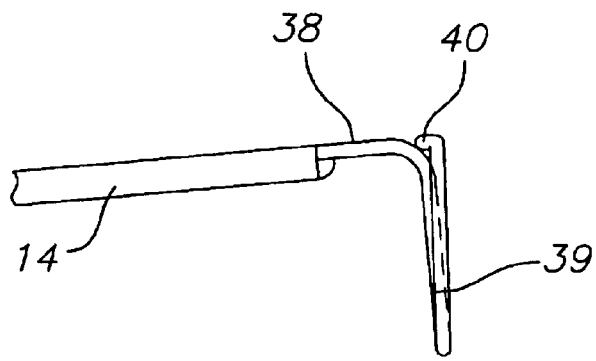
FIG. 6 is a side view of the ablation assembly of FIG. 5.

In an alternative embodiment, as shown in FIGS. 5 and 6, the ablation assembly 17 further comprises a generally straight distal region 40 that extends beyond the generally circular main region 39. In this embodiment, the proximal region 38 is at the side of the generally circular main region 39, as best shown in FIG. 6.

The support member 24 is made of a material having shape-memory, i.e., that can be straightened or bent out of its original shape upon exertion of a force and is capable of substantially returning to its original shape upon removal of the force. A particularly preferred material for the support member 24 is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. The non-conductive covering 28 can be made of any suitable material, and is preferably made of a biocompatible plastic such as polyurethane or PEBAX. If desired, the support member 24 can be eliminated and the distal end of the non-conductive covering 28 can be preformed to have the desired curve of the ablation assembly.

Figure 7:
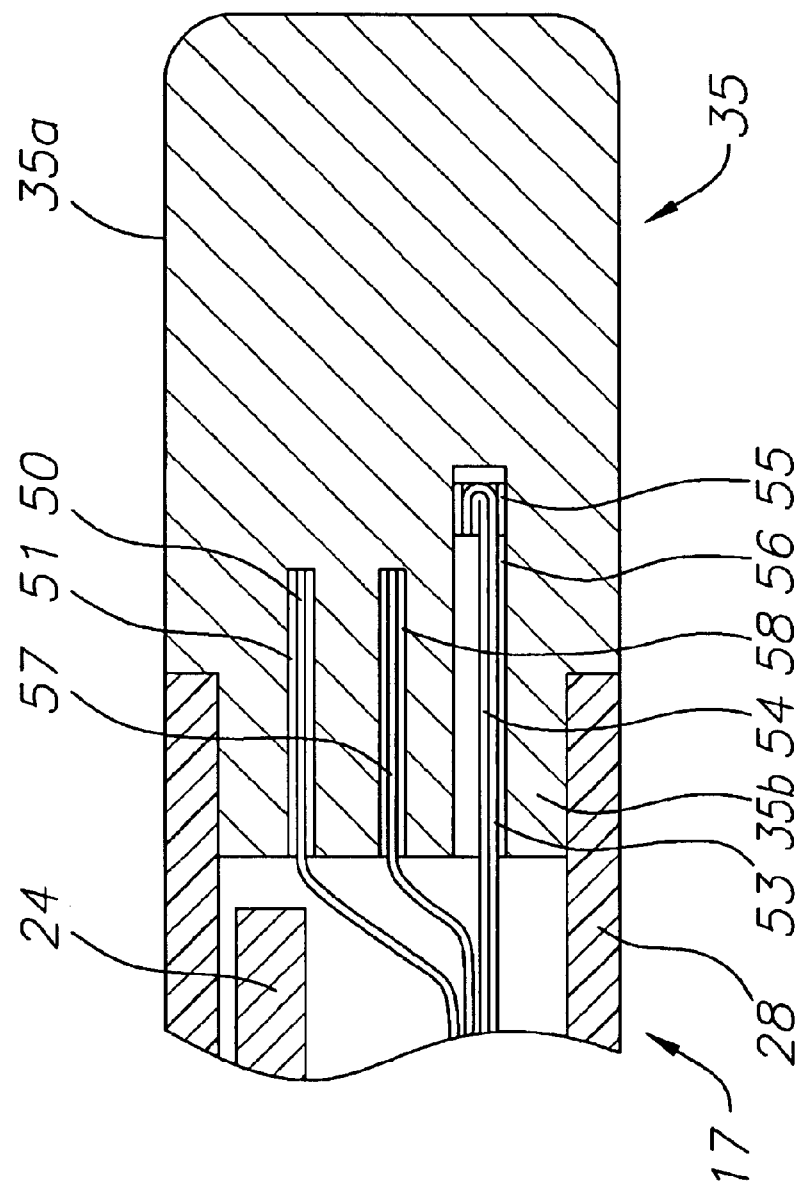
FIG. 7 is a side cross-sectional view of the distal end of an ablation assembly according to the invention.

A tip electrode 35 is mounted at the distal end of the ablation assembly 17 for ablating tissue. As shown in FIG. 7, the tip electrode 35 has an exposed region 35a and a stem 35b that extends into the non-conductive covering 28. In the embodiment of FIG. 7, the tip electrode 35 has a generally cylindrical exposed region 35a with an outer diameter approximately the same as the outer diameter of the non-conductive covering 28 along essentially the entire length of the exposed region. The stem 35b is preferably fixed to the inside of the non-conductive covering 28 by polyurethane glue or the like.

Figure 8:
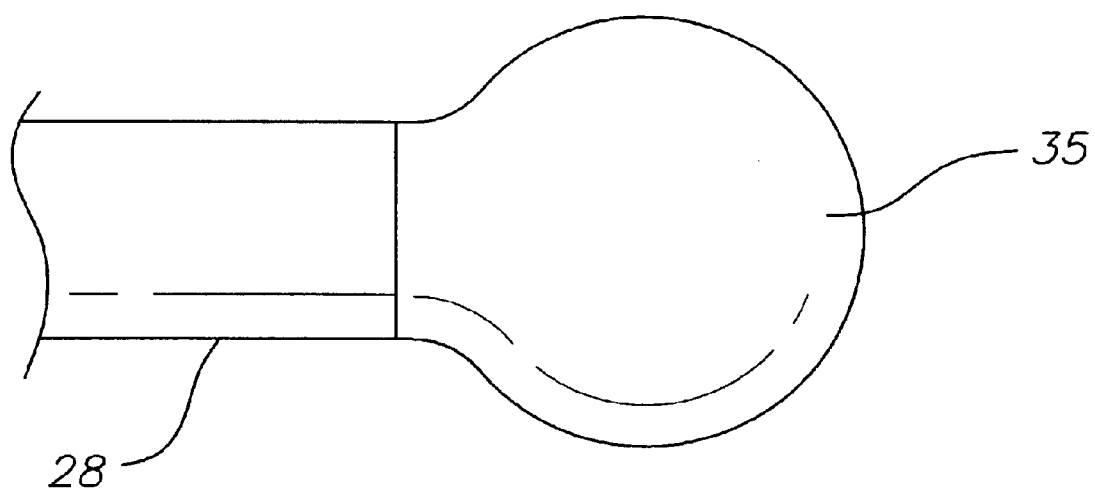
FIG. 8 is a perspective view of an alternative tip electrode according to the invention.
Figure 9:
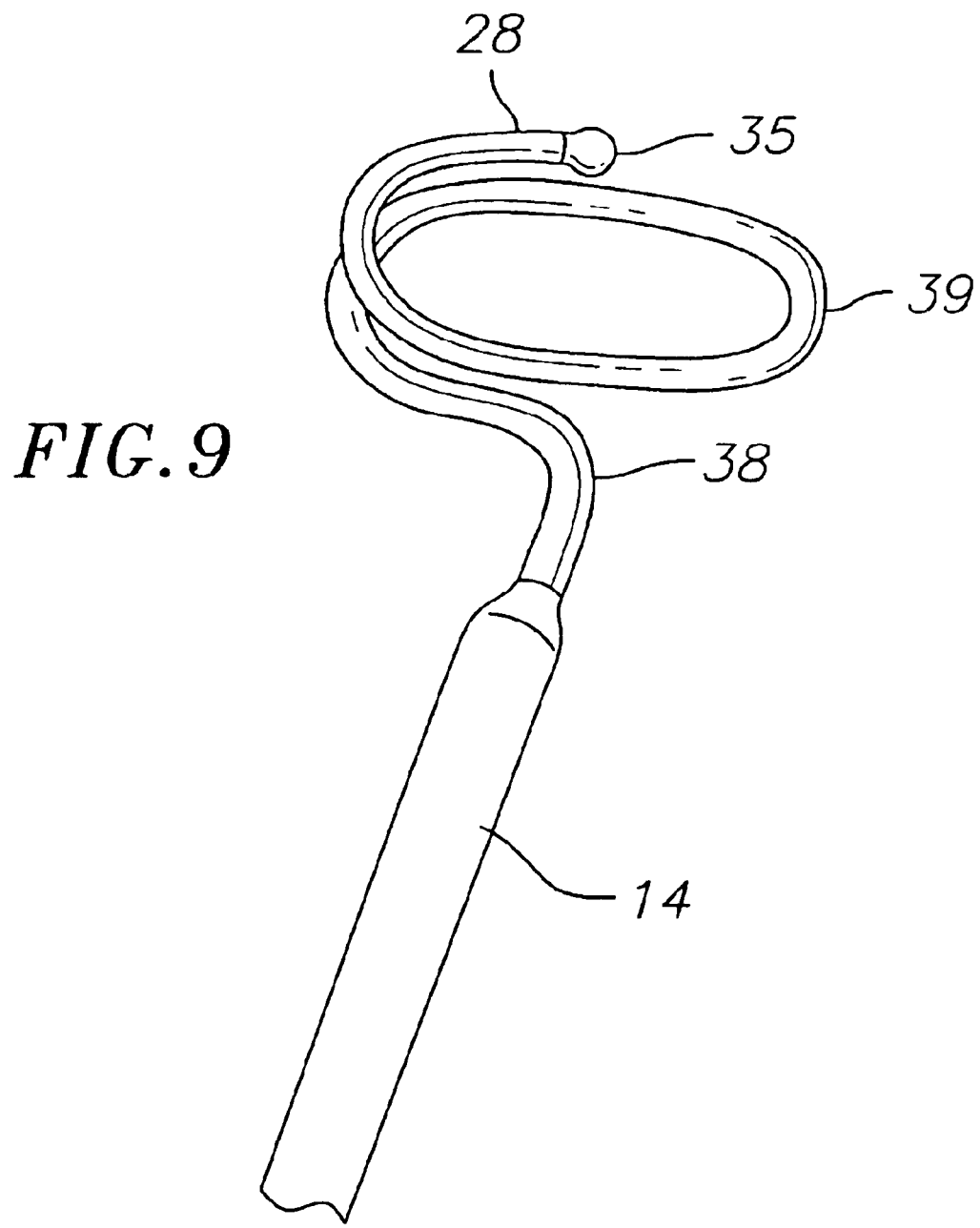
FIG. 9 is a schematic perspective view of an ablation assembly with the alternative tip electrode of FIG. 8.

In an alternative embodiment, as shown in FIG. 8, the exposed region 35a of the tip electrode has a bulb shape with a varying outer diameter wherein at least a portion of the exposed region extends beyond the outer circumference of the non-conductive covering 28. It has been found that a catheter having a bulb-shaped tip electrode can provide better contact with the tissue based on the outward spring-like force exerted by the generally circular ablation assembly. Other tip electrode shapes will be apparent to one skilled in the art. For example, an asymmetrical tip electrode (not shown) could be provided where the side of the electrode that would be in contact with the tissue, i.e., on the outside of the ablation assembly, extends beyond the outer wall of the non-conductive covering 28 and the inner side of the tip electrode is generally even with the wall of the non-conductive covering.

An electrode lead wire 50 connects the tip electrode 35 to a suitable source of ablation energy (not shown), preferably radio frequency (RF) energy. The distal end of the lead wire 50 is soldered in a first blind hole 51 in the proximal end of the tip electrode 35. The lead wire 50 extends between the non-conductive covering 28 and the support member 24. The proximal end of the lead wire 50 is electrically connected to a suitable connector 37, which is connected to the source of ablation energy as is known in the art. The lead wire 50 extends through the first lumen 30 of the intermediate section 14, the central lumen 18 of the catheter body 12, and the control handle 16, and terminates at its proximal end in the connector 37. In the depicted embodiment, the portion of the lead wire 50 extending through the central lumen 18 of the catheter body 12, control handle 16 and proximal end of the intermediate section 14 is enclosed within a protective sheath 62 to prevent contact with other components within the lumen of catheter body and in the handle. The protective sheath 62 can be made of any suitable material, preferably polyimide. The protective sheath 62 is anchored at its distal end to the proximal end of the intermediate section 14 by gluing it in the first lumen 30 with polyurethane glue or the like. As would be recognized by one skilled in the art, the protective sheath can be eliminated if desired.

A temperature sensor is provided for monitoring the temperature of the tip electrode 35. Any conventional temperature sensor, e.g., a thermocouple or thermistor, may be used. In the embodiment shown in FIG. 7, the temperature sensor comprises a thermocouple formed by an enameled wire pair. One wire of the wire pair is a copper wire 53, e.g., a number 40 copper wire. The other wire of the wire pair is a constantan wire 54. The wires 53 and 54 of the wire pair are electrically isolated from each other except at their distal ends where they are twisted together, covered with a short piece of plastic tubing 55, e.g., polyimide, and covered with epoxy. The plastic tubing 55 is then attached in a second blind hole 56 of the tip electrode 35, by polyurethane glue or the like. Alternatively, the wires 53 and 54 can be soldered into the second blind hole 56 or otherwise attached to the tip electrode 35. The wires 53 and 54 extend through the first lumen 30 in the intermediate section 14 and through the central lumen 18 of the catheter body 12 along with the lead wire 50. The wires 53 and 54 then extend out through the control handle 16 and to a connector (not shown) connectable to a temperature monitor (not shown). Preferably the wires 53 and 54 extend through the protective sheath 62 in the catheter body 12.

Additionally, a safety wire 57 is provided to further secure the tip electrode 35 to the ablation assembly 17 and assure that the tip electrode does not fall off in the patient's body. The safety wire is preferably a metal wire having its distal end soldered in a third blind hole 58 in the tip electrode 35 and its proximal end soldered or otherwise attached in the control handle 16. In the depicted embodiment, the safety wire 57 extends through the first lumen 30 in the intermediate section 14 and through the central lumen 18 of the catheter body 12 along with the lead wires 50 and thermocouple wires 53 and 54. Other arrangements for attaching the safety wire can be provided, as would be recognized by one skilled in the art, or the safety wire can be eliminated.

If desired, one or more ring electrodes (not shown) can be mounted on the non-conductive covering 28 of the generally circular main region 39 of the ablation assembly 17. Such ring electrodes might be desirable, for example, for mapping the region to be ablated before ablation begins or after ablation to assure that the lesions blocked the electrical activity as desired. A description of a catheter including such ring electrodes is described in U.S. patent application Ser. No. 09/551,467, entitled "Catheter Having Mapping Assembly," the entire disclosure of which is incorporated herein by reference. If desired, additional ring electrodes (not shown) could be mounted elsewhere along the ablation assembly 17 and/or intermediate section 14.

The junction of the intermediate section 14 and ablation assembly 17 is shown in FIG. 3. The non-conductive covering 28 is attached to the tubing 22 of the intermediate section by glue or the like. The support member 24 extends from the third lumen 34 into the non-conductive covering 28. The proximal end of the support member 24 terminates a short distance within the third lumen 34, approximately about 5 mm, so as not to adversely affect the ability of the intermediate section 14 to deflect. However, if desired, the proximal end of the support member 24 can extend into the catheter body 12.

The lead wire 50, thermocouple wires 53 and 54 and safety wire 57 extend through the first lumen 30 of the intermediate section 14, through the central lumen 18 of the catheter body 12, and the control handle 16, and terminate at their proximal end in the connector 37. As noted above, the portion of the wires extending through the central lumen 18 of the catheter body 12, control handle 16 and proximal end of the intermediate section 14 are enclosed within a protective sheath 62, which can be made of any suitable material, preferably polyimide. The protective sheath 62 is anchored at its distal end to the proximal end of the intermediate section 14 by gluing it in the first lumen 30 with polyurethane glue or the like.

The puller wire 64 is provided for deflection of the intermediate section 14. The puller wire 64 extends through the catheter body 12, is anchored at its proximal end to the control handle 16, and is anchored at its distal end to the intermediate section 14. The puller wire 64 is made of any suitable metal, such as stainless steel or Nitinol, and is preferably coated with Teflon® or the like. The coating imparts lubricity to the puller wire 64. The puller wire 64 preferably has a diameter ranging from about 0.006 to about 0.010 inch.

A compression coil 66 is situated within the catheter body 12 in surrounding relation to the puller wire 64, as shown in FIG. 2. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. The outer surface of the compression coil 66 is covered by a flexible, nonconductive sheath 68, e.g., made of polyimide tubing.

The compression coil 66 is anchored at its proximal end to the outer wall 20 of the catheter body 12 by proximal glue joint 70 and at its distal end to the intermediate section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

The puller wire 64 extends into the second lumen 32 of the intermediate section 14. Preferably the puller wire 64 is anchored at its distal end to the distal end of the intermediate section 14, as shown in FIG. 3. Specifically, a T-shaped anchor is formed, which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a cross-piece 82 formed of stainless steel ribbon or the like. The cross-piece 82 sits beyond the distal end of the second lumen 32. The cross-piece 82 is larger than the lumen opening and, therefore, cannot be pulled through the opening. The distal end of the second lumen 32 is then filled with glue or the like, preferably a polyurethane glue. Within the second lumen 32 of the intermediate section 14, the puller wire 64 extends through a plastic, preferably Teflon®, puller wire sheath (not shown), which prevents the puller wire 64 from cutting into the wall of the intermediate section 14 when the intermediate section is deflected.

Longitudinal movement of the puller wire 64 relative to the catheter body 12, which results in deflection of the intermediate section 14, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

In use, a suitable guiding sheath is inserted into the patient with its distal end positioned at a desired mapping location. An example of a suitable guiding sheath for use in connection with the present invention is the Preface™ Braided Guiding Sheath, commercially available from Biosense Webster, Inc. (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the ablation assembly 17 is straightened to fit through the sheath. Once the distal end of the catheter is positioned at the desired mapping location, the guiding sheath is pulled proximally, allowing the deflectable intermediate section 14 and ablation assembly 17 to extend outside the sheath, and the ablation assembly 17 returns to its original shape. The ablation assembly 17 is then inserted into a pulmonary vein or other tubular region (such as the coronary sinus, superior vena cava, or inferior vena cava) so that the outer circumference of the generally circular main region 39 of the assembly is in contact with a circumference inside the tubular region and the tip electrode 35 is generally in contact with the tissue.

The circular arrangement of the ablation assembly 17 provides a stable mechanism for keeping the tip electrode 35 in a desired location for ablation. To ablate a circumferential lesion in the tubular region, the user rotates the ablation assembly 17 by rotating the control handle 16 and applies ablation energy through the tip electrode 35 at adjacent points along the circumference. The design of the ablation assembly permits the user to more easily ablate about a circumference compared to using a tip electrode on a straight catheter, where it is more difficult to accurately move the tip electrode about the circumference of the tubular region.

As will be recognized by one skilled in the art, it is easier to turn the ablation assembly in a direction such that the tip electrode is being pulled rather than pushed. For example, in the embodiments depicted in FIGS. 4 and 5, where the ablation assemblies are formed in a clockwise direction, it is preferable to turn the assemblies in a counterclockwise direction. Accordingly, if desired an arrow or other indicator (not shown) can be included on the handle or proximal end of the catheter body to indicate to the user the preferred direction for rotating the ablation assembly in the body.

If desired, two or more puller wires can be provided to enhance the ability to manipulate the intermediate section. In such an embodiment, a second puller wire and a surrounding second compression coil extend through the catheter body and into an additional off-axis lumen in the intermediate section. The first puller wire is preferably anchored proximal to the anchor location of the second puller wire. Suitable designs of catheters having two or more puller wires, including suitable control handles for such embodiments, are described, for example, in U.S. Pat. Nos. 6,123,699, 6,171,277, 6,183,435, 6,183,463, 6,198,974, 6,210,407, and 6,267,746, the disclosures of which are incorporated herein by reference.

Alternatively, a second puller wire (not shown) can be included to alter the diameter of the distal end of the ablation assembly. Such an arrangement is generally described in U.S. Pat. No. 5,626,136, the disclosure of which is incorporated herein by reference. The above-referenced control handles could be used to manipulate the second puller wire.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for ablating tissue within a tubular region of or near the heart having a inner circumference, the method comprising:

inserting into the heart a distal end of a catheter comprising:
   an elongated tubular catheter body having proximal and distal ends, an axis, and at least one lumen extending therethrough; and
   an ablation assembly at the distal end of the tubular body having a preformed generally circular curve having an outer circumference and being generally transverse to the axis of the catheter body, the ablation assembly comprising a generally circularly curved flexible tubing having proximal and distal ends, the flexible tubing carrying a tip electrode at its distal end, the tip electrode being generally bulb-shaped;

contacting at least a portion of the outer circumference of the generally circular curve with the inner circumference of the tubular region so that the tip electrode is in a first position in contact with tissue along the inner circumference;

ablating tissue at the first position with the tip electrode;

rotating the ablation assembly so that the tip electrode is in a second position in contact with tissue along the inner circumference different from the first position; and ablating tissue at the second position with the tip electrode.

2. A method according to claim 1, wherein the tubular region is selected from the group consisting of pulmonary veins, the coronary sinus, the superior vena cava, and the inferior vena cava.

3. A method according to claim 1, wherein the tubular region is a pulmonary vein.

4. A method according to claim 1, wherein at least a portion of the exposed region has an outer diameter greater than the outer diameter of the flexible tubing of the ablation assembly.

5. A method according to claim 1, wherein the generally circular curve has an outer diameter ranging from about 10 mm to about 25 mm.

6. A method according to claim 1, wherein the generally circular curve has an outer diameter ranging from about 12 mm to about 20 mm.

7. A method according to claim 1, wherein the generally circular curve is at least about 320°.

8. A method according to claim 1, wherein the generally circular curve is at least about 360°.

9. A method according to claim 1, wherein the generally circular curve consists of a single generally circular curve.

10. A method according to claim 1, wherein the ablation assembly further comprises a support member comprising a material having shape memory extending through at least a portion of the flexible tubing.

11. A method according to claim 1, further comprising an intermediate section disposed between the catheter body and the ablation assembly, the intermediate section having at least one lumen extending therethrough and being more flexible than the catheter body.

12. A method for ablating tissue within a tubular region of or near the heart having a inner circumference, the method comprising:

inserting into the heart a distal end of a catheter comprising:
an elongated tubular catheter body having proximal and distal ends, an axis, and at least one lumen extending therethrough; and
an ablation assembly at the distal end of the tubular body having a preformed generally circular curve having an outer circumference and an outer diameter ranging from about 10 mm to about 25 mm, the ablation assembly being generally transverse to the axis of the catheter body and comprising a generally circularly curved flexible tubing having proximal and distal ends, the flexible tubing carrying a tip electrode at its distal end, wherein the tip electrode has an exposed region that is generally bulb-shaped and that has an outer diameter greater than the outer diameter of the flexible tubing of the ablation assembly;

contacting at least a portion of the outer circumference of the generally circular curve with the inner circumference of the tubular region so that the tip electrode is in a first position in contact with tissue along the inner circumference;

ablating tissue at the first position with the tip electrode;

rotating the ablation assembly so that the tip electrode is in a second position in contact with tissue along the inner circumference different from the first position; and ablating tissue at the second position with the tip electrode.

13. A method for ablating tissue within a tubular region of or near the heart having a inner circumference, the method comprising:

inserting into the heart a distal end of a catheter comprising:
an elongated tubular catheter body having proximal and distal ends, an axis, and at least one lumen extending therethrough; and
an ablation assembly at the distal end of the tubular body having a preformed generally circular curve having an outer circumference and being generally transverse to the axis of the catheter body, the ablation assembly comprising a generally circularly curved flexible tubing having proximal and distal ends, the flexible tubing carrying a tip electrode at its distal end, wherein the tip electrode is generally bulb-shaped;

contacting at least a portion of the outer circumference of the generally circular curve with the inner circumference of the tubular region so that the tip electrode is in a first position in contact with tissue along the inner circumference; and ablating tissue at the first position with the tip electrode.

14. A method according to claim 13, wherein the tubular region is selected from the group consisting of pulmonary veins, the coronary sinus, the superior vena cava, and the inferior vena cava.

15. A method according to claim 13, wherein the tubular region is a pulmonary vein.

16. A method according to claim 13, wherein the generally circular curve has an outer diameter ranging from about 10 mm to about 25 mm.

17. A method according to claim 13, wherein the generally circular curve has an outer diameter ranging from about 12 mm to about 20 mm.

18. A method according to claim 13, wherein the generally circular curve is at least about 320°.

19. A method according to claim 13, wherein the generally circular curve is at least about 360°.

20. A method according to claim 13, wherein the generally circular curve consists of a single generally circular curve.

* * * * *